United States Patent
Basler

(10) Patent No.: US 8,622,668 B2
(45) Date of Patent: Jan. 7, 2014

(54) MACHINING DEVICE, PARTICULARLY FOR THE PRODUCTION OF TOOTH REPLACEMENT PARTS OR MODELS THEREOF

(75) Inventor: Franz Basler, Spatburgunderhof (DE)

(73) Assignee: Sirona Dental Systems GmbH, Bensheim (DE)

( * ) Notice: Subject to any disclaimer, the term of this patent is extended or adjusted under 35 U.S.C. 154(b) by 1038 days.

(21) Appl. No.: 12/438,323

(22) PCT Filed: Aug. 23, 2007

(86) PCT No.: PCT/EP2007/058755
§ 371 (c)(1),
(2), (4) Date: Feb. 20, 2009

(87) PCT Pub. No.: WO2008/023043
PCT Pub. Date: Feb. 28, 2008

(65) Prior Publication Data
US 2009/0290948 A1    Nov. 26, 2009

(30) Foreign Application Priority Data

Aug. 24, 2006    (DE) .......................... 10 2006 039 618

(51) Int. Cl.
*B23Q 11/08*    (2006.01)
*B23Q 11/10*    (2006.01)
*B23C 1/14*    (2006.01)

(52) U.S. Cl.
USPC ........... 409/134; 409/136; 409/137; 409/167; 409/168; 409/172

(58) Field of Classification Search
USPC ......... 409/134, 136, 137, 164, 165, 167, 168, 409/172, 221, 224; 82/15, 70, 157, 162
IPC .......................... B23Q 11/08,11/10; B23C 1/14
See application file for complete search history.

(56) References Cited

U.S. PATENT DOCUMENTS

| | | | | |
|---|---|---|---|---|
| 2,681,596 | A * | 6/1954 | Klomp | 409/165 |
| 3,173,336 | A * | 3/1965 | Cull | 409/193 |
| 3,187,635 | A * | 6/1965 | Koss | 409/192 |
| 4,858,290 | A * | 8/1989 | Hirose et al. | 29/35.5 |
| 5,078,256 | A * | 1/1992 | Hatano et al. | 198/360 |
| 5,113,558 | A * | 5/1992 | Soroka et al. | 29/57 |
| 5,263,800 | A * | 11/1993 | Chen | 409/137 |
| 5,294,220 | A * | 3/1994 | Ohmstede et al. | 409/137 |
| 5,586,848 | A * | 12/1996 | Suwijn | 409/137 |
| 5,660,509 | A * | 8/1997 | Cole et al. | 409/81 |
| 5,669,867 | A * | 9/1997 | Hoppe | 483/55 |
| 6,364,582 | B1 * | 4/2002 | Hoppe et al. | 409/134 |

(Continued)

FOREIGN PATENT DOCUMENTS

| | | |
|---|---|---|
| DE | 199 28 002 C1 | 10/2000 |
| DE | 100 19 669 A1 | 10/2001 |

(Continued)

*Primary Examiner* — Eric A Gates
(74) *Attorney, Agent, or Firm* — Fitzpatrick, Cella, Harper & Scinto

(57) ABSTRACT

Disclosed is a machining device, particularly for producing tooth replacement parts or models thereof, comprising a workpiece holder and at least one machining tool which is disposed in a machining space for a workpiece that is mounted therein. The feeding axis for the workpiece into the machining space extends at an angle relative to the horizontal.

7 Claims, 2 Drawing Sheets

(56) References Cited

U.S. PATENT DOCUMENTS

| | | | |
|---|---|---|---|
| 6,394,880 B1 | 5/2002 | Basler et al. | 451/28 |
| 6,571,670 B2 * | 6/2003 | Chang | 82/152 |
| 7,220,087 B2 * | 5/2007 | Sugata et al. | 409/132 |
| 7,493,681 B2 * | 2/2009 | Schmidt et al. | 29/26 A |
| 8,087,858 B2 * | 1/2012 | Martin | 409/221 |
| 2012/0087757 A1 * | 4/2012 | Basler | 409/132 |

FOREIGN PATENT DOCUMENTS

| | | | |
|---|---|---|---|
| EP | 0 455 853 A1 | 11/1991 | |
| EP | 0 455 853 B1 | 4/1995 | |
| JP | 58-171229 | 10/1983 | |
| JP | 2003071663 A * | 3/2003 | B23Q 1/00 |
| WO | 03/061903 A1 | 7/2003 | |

\* cited by examiner

MACHINING DEVICE, PARTICULARLY FOR THE PRODUCTION OF TOOTH REPLACEMENT PARTS OR MODELS THEREOF

This Application is a National Stage filing under 35 U.S.C. §371 of International Application No. PCT/EP2007/058755, filed Aug. 23, 2007, which in turn claims the benefit of priority based on German Patent Application No. 10 2006 039 618.9, filed Aug. 24, 2006, each of which is incorporated by reference herein in its entirety, as is fully set forth herein. International Application No. PCT/EP2007/058755 has been published in German, but not English, as International Publication No. WO 2008/023043A1, on Feb. 28, 2008.

The invention relates to a machining device, particularly for the production of dental replacement parts or models thereof. The machining device comprises a workpiece holder and at least one machining tool, which together form a machining chamber for a workpiece mounted therein.

PRIOR ART

EP 0 455 853 B1 discloses a machining device for the production of dental replacement parts, in which machining device the feed axis of the workpiece is located horizontally in the machining chamber.

DE 199 28 002 C1 discloses a tabletop unit in a horizontal configuration. Due to the horizontal disposition of the workpiece axis, the space requirements in terms of depth increase relatively to the size of the machining chamber, and the quantity of coolant accommodated is limited due to the flat construction.

It is an object of the present invention to provide a machining device, particularly for the production of dental replacement parts or models thereof, which comprises an enlarged machining chamber and thus makes it possible to fabricate large dental restorations. The present invention is thus intended to make allowance for the space available in the dental premises and in the dental laboratory, in particular the depth dimension of the table and the height available between the table and the wall units. The standard depth dimension of the table is between 0.5 m and 0.6 m; the available height is usually between 0.4 m and 0.6 m.

SUMMARY OF THE INVENTION

A machining device of the invention, particularly for the production of dental replacement parts or models thereof, comprises a workpiece holder and at least one machining tool disposed in a machining chamber for a workpiece mounted therein, in which the feed axis of the workpiece as it travels into the machining chamber is inclined at an angle to the horizontal.

The inclination of the feed axis is such that the workpiece is situated above the workpiece holder. This therefore results in a negative angle relative to the horizontal.

The arrangement of the feed axis of the workpiece at a downward slant from the horizontal permits a minimization in the space requirements of the machining device so that the depth and height of the housing can be restricted to dimensions that correspond to standard dimensions of the device in dental premises and in the dental laboratory. At the same time, very large restorations can be fabricated, since the slant makes it possible to provide the machining chamber with larger dimensions while the depth of the housing remains the same. A feed axis inclined at an angle of 45° results in a feed path that is longer by a factor of 1.41, while the depth of the machining chamber remains unchanged.

Due to the inclined disposition of the feed axis, the workpiece axis is disposed away from the sump composed of coolant and the swarf formed in the machining chamber, so that the bearings of the workpiece axis do not come into contact with the coolant.

The inclined disposition of the workpiece axis further makes it possible to insert the workpiece into the workpiece holder in a direction akin to the direction of view.

It has been found that it is not at all easy to insert a workpiece into a horizontally or vertically aligned chuck. The inclined arrangement thus results in faster positioning of the workpiece against the chuck, and the time taken to load the machining device is reduced.

Advantageously, the angle of inclination can range from 30 to 60 degrees and is preferably 45 degrees. This enables a compromise to be reached between the space requirements in terms of depth and the space requirements in terms of height.

Advantageously, the machining chamber is disposed in a housing enclosing the at least one machining tool and its holder, the workpiece holder and its guide, and a machine bed. A compact device can thus be provided which has smooth surfaces and can be easily cleaned.

Advantageously, the machine bed can be disposed in the housing in a slanting configuration, and a container for the coolant can be provided below the machining chamber and in front of the machine bed, which simplifies draining of the coolant from the machining chamber. Furthermore, the slant allows for the use of a container for the coolant having a sufficiently large volume and of appropriate height, which makes for improved settling behavior of the swarf and thus increases the time interval to exchange the container.

Advantageously, the machining device can be in the form of a tabletop unit.

It is particularly advantageous when the machining device comprises a cover that surrounds the machining chamber over an arc of at least 150 degrees. A cover having such an opening angle makes it possible to observe the machining process from the front and rear sides.

Advantageously, a storage space is provided in the housing laterally below the machining chamber, which storage space is accessible from the front of the housing. The inclined disposition of the workpiece axis thus provides additional space in the housing laterally below the machining chamber where, for example, drawers can be mounted for accommodating accessories.

BRIEF DESCRIPTION OF THE DRAWING

The drawing shows an exemplary embodiment of the invention, in which.

EXEMPLARY EMBODIMENT

Figure 1:
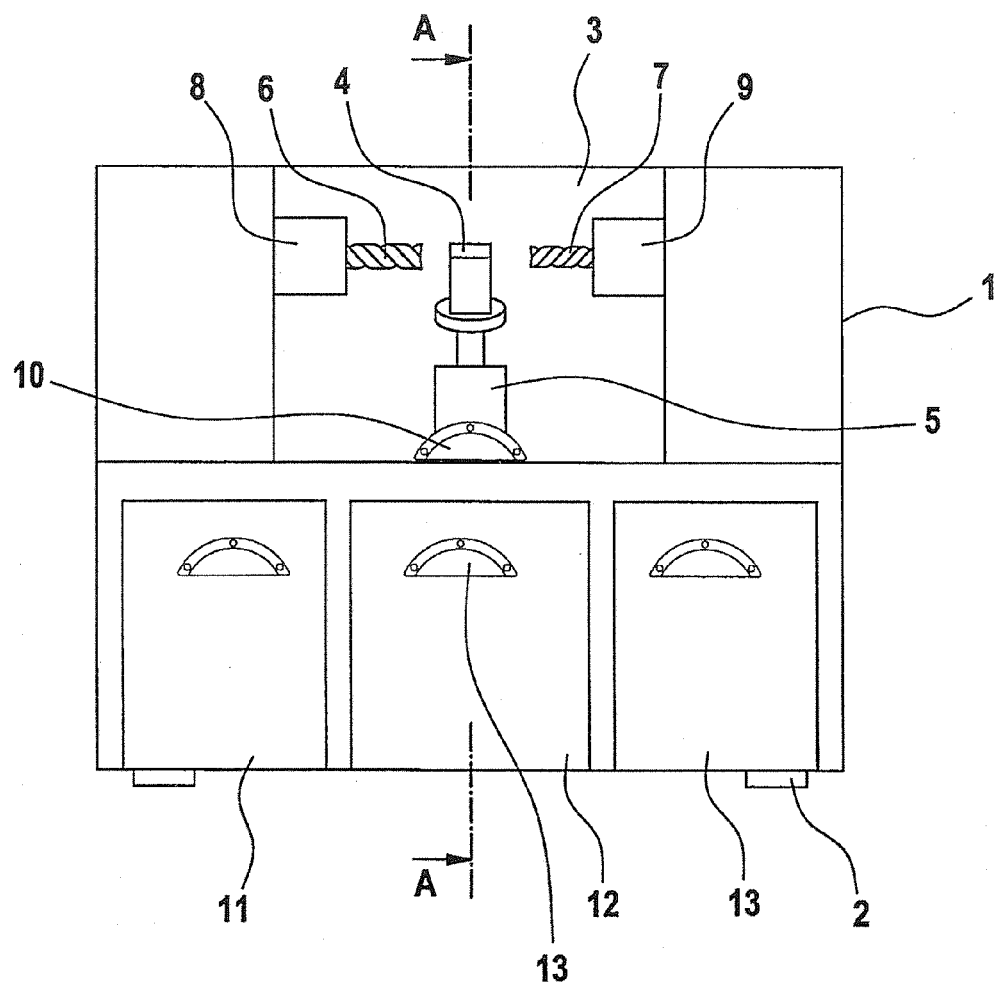
FIG. 1 is a front view of a machining device formed as a tabletop unit.

The machining device shown in front view in FIG. 1 is in the form of a tabletop unit; that is to say, this machining device is placed on an existing table (not shown) or worktop. The machining device comprises a housing 1, to which vertically adjustable feet 2 are attached for setting up and aligning the machining device on a firm support. In the upper half of the housing there is provided a machining chamber 3, which is disposed approximately centrally in the housing 1. In the machining chamber 3 there is shown a workpiece 4, which is replaceably mounted in a workpiece holder 5. Inside the machining chamber 3 there is deposed a machining tool 6, 7 on each side of the workpiece 4, each of the machining tools 6, 7 being mounted in a tool holder 8 and 9 respectively.

The machining chamber 3 is closed by a cover 35 (FIG. 2), of which only the handle 10 is shown. The cover itself is transparent and pivots about an axis, which is located in a plane extending parallel to the plane of the drawing. This will be explained in greater detail below.

The guides and drives for the tool holders 8, 9 are disposed laterally next to the machining chamber 3, but these guides and drives are hidden by the closed housing 1.

In the lower portion of the housing 1 there can be provided drawers or flaps 11 to 13 which are accessible from the front. For this purpose, a handle 14 is provided on the drawer 12, for example.

Figure 2:
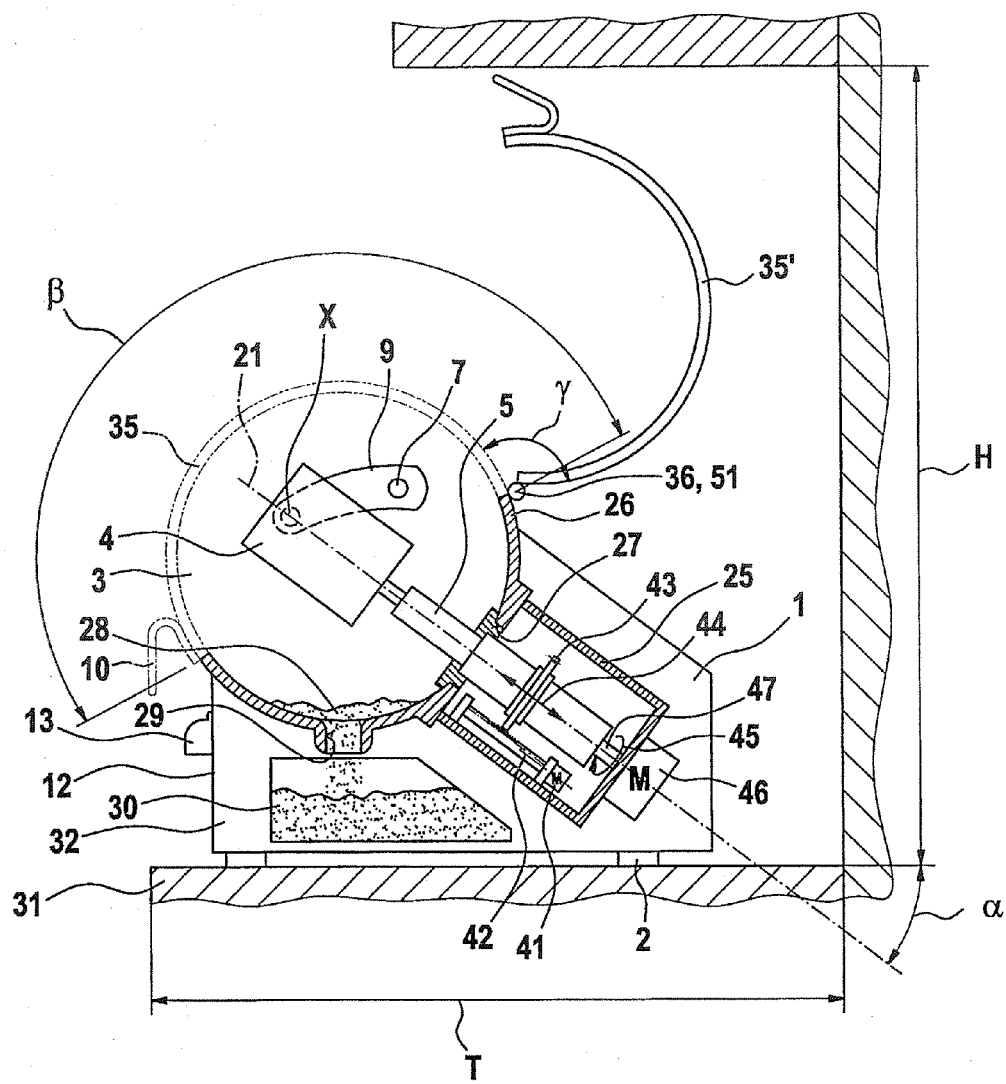
FIG. 2 shows a cross section of the machining device of FIG. 1 taken along line A-A marked in FIG. 1.

FIG. 2 shows a cross-section of the machining device shown in FIG. 1 taken along line A-A. In the machining chamber 3, the workpiece 4 is disposed in a workpiece holder and can be displaced along a feed axis 21. As the workpiece 4 is displaced along the feed axis 21, the workpiece 4 is guided past the machining tool 7, and the machining tool 7 can be adjusted on the tool holder 9 relatively to the workpiece 4.

The tool 7 and the tool holder 9 can be designed as a four-axis system. In the present case, it would then be possible to move the tool 7 toward and away from the workpiece 4 as well as transversely or obliquely to the feed axis 21 along the workpiece 4, for instance, by swiveling the tool holder 9 about the axis of rotation X. The same applies to the machining tool (not shown) disposed on the other side of the workpiece 4.

Furthermore, provision can be made for the workpiece holder 5 and thus the workpiece 4 mounted therein to rotate about the feed axis 21, for instance, in order to be able to produce undercuts in this spatial direction. For this purpose, a motor 41 is provided, which drives a rod 42 that has external teeth and is mounted in the machine bed and in turn drives a gear 43, which is non-rotatably connected to the workpiece holder 5. Even in the case of longitudinal displacement of the workpiece holder 5 in the direction of the feed axis 21, i.e. along the arrow 44, the length of the rod 42 is such that rotation of the workpiece holder 5, as shown by the arrow 45, is possible.

The feed of the workpiece 4 along the feed axis 21 is brought about by insertion of the workpiece holder 5 into the machining chamber 3 caused by a drive 46 adapted to drive a spindle 47 guided inside the workpiece holder in a spindle nut (not shown).

The workpiece holder 5 is mounted in a machine bed 25, which merges into a boundary wall 26 of the machining chamber 3. The workpiece holder 5 is sealed from the machining chamber 3 in the region of the opening in the machining chamber 3 so that no coolant, chipping or swarf can pass from the machining chamber 3 into the machine bed 25. This opening 27 is at a higher position than the coolant sump 28 and an aperture 29 in the boundary wall 26.

The coolant sump 28 can flow through the aperture 29 in the boundary wall 26 into a container 30 disposed below the machining chamber 3, which container 30 is disposed in front of the machine bed 25 and can be removed from the housing 1 by way of a flap 12, which can be opened using the handle 13.

The coolant container can cooperate with a pump (not shown), in order to recycle the coolant collected in the container 30 in filtered form into the machining chamber 3. This pump can be disposed, for example, in the drawer 11 (FIG. 1) and to the side of the machine bed.

The machining device stands with its housing 1 on a horizontal plate 31. The feed axis 21 is inclined by an angle α of from 30° to 60°, preferably 45° relative to the horizontal plane of the plate. This arrangement ensures, on the one hand, that the workpiece holder 5 is not located in the coolant sump 28 and, on the other hand, that a sufficiently large container 30 can be provided for the coolant.

Furthermore, given heights H and depths T are taken into account.

The machining chamber 3 is closed by a cover 35, which can be swiveled about a hinge joint 36 by means of the handle 10. The cover 35 can extend, as shown in the exemplary embodiment, through an angle β of more than 180° and can be opened through an angle γ about its swivel joint 51. The cover section that extends beyond 180° does not follow the circular arc, but rather extends not more than tangentially to the circular arc. The opening angle γ is between 80° and 110°.

After the cover 35 has been opened, the workpiece holder 5 is accessible from the front of the housing 1 (from the left of the drawing) and the machined workpiece 4 can be removed from the inclined workpiece holder 5, and a new workpiece inserted. Due to the inclined disposition of the workpiece holder 5, the insertion of the new workpiece is effected in the direction of movement of the operator, thereby facilitating "threading" of the workpiece 4 into the workpiece holder 5.

By virtue of the fact that the cover 35 can extend from a point in front of the front side of the housing 1 to the rear side of the housing 1, the machining process can be watched and monitored from both sides.

The machine bed 25 and the boundary wall 26 connected thereto are held firm in the housing 1. For this purpose, the housing 1 is attached at suitable locations to the machine bed 25 and to the boundary wall 26, for example, by screws.

The vertically adjustable feet 2 can be formed in such a way that the transmission of vibrations, whether mechanical or acoustic, to the plate 31 is damped.

The container 30 is accommodated in a storage space 32, which can extend below the machining chamber 3 and in front of the machine bed 25 over the width of the housing 1 and is however located at least directly below the machining chamber 3. In this storage space it is also possible to accommodate small parts in addition to the container 30 for the coolant, for example, with the help of drawers or flaps comprising removable inserts.

An aperture 29 leading to the container 30 located below the machining chamber is provided at the lowest point of the machining chamber.

The invention claimed is:

1. A machining device for producing dental replacement parts or models of dental replacement parts, the device comprising:
 a machining chamber in which a workpiece is machined, wherein a feed axis of said workpiece as the workpiece travels in said machining chamber is inclined at an angle from 30 to 60 degrees relative to a horizontal plane;
 a workpiece holder for holding the workpiece in the machining chamber as the workpiece is displaced along the feed axis, at least one of the workpiece and workpiece holder being rotatable about the feed axis; and
 a machining tool disposed in said machining chamber, wherein the workpiece is guided past the machining tool as the workpiece is displaced along the feed axis, wherein said machining chamber is disposed in a housing including said machining tool and a holder of said machining tool and also said workpiece holder and a machine bed, and wherein said machine bed is disposed in a slanting position in said housing and, wherein a container for a coolant is provided below said machining chamber and in front of said machine bed.

2. The machining device as defined in claim 1, wherein said angle is 45 degrees.

3. The machining device as defined in claim 1, wherein said device is a tabletop device.

4. The machining device as defined in claim 1, wherein said housing includes a cover surrounding said machining chamber over an arc of at least 150 degrees.

5. The machining device as defined in claim 1, wherein a storage space is present in said housing laterally below said machining chamber and is accessible from the front of said housing.

6. The machining device according to claim 1, wherein the workpiece holder is mounted in a machine bed which merges into a boundary wall of the machining chamber.

7. The machining device according to claim 1, wherein the workpiece holder is sealed from the machining chamber.

* * * * *

UNITED STATES PATENT AND TRADEMARK OFFICE
CERTIFICATE OF CORRECTION

| | | |
|---|---|---|
| PATENT NO. | : 8,622,668 B2 | Page 1 of 1 |
| APPLICATION NO. | : 12/438323 | |
| DATED | : January 7, 2014 | |
| INVENTOR(S) | : Franz Basler | |

It is certified that error appears in the above-identified patent and that said Letters Patent is hereby corrected as shown below:

ON THE TITLE PAGE ITEM (75) INVENTOR:

"Franz Basler, Spatburgunderhof (DE)" should read --Franz Basler, Laudenbach (DE)--.

Signed and Sealed this
Twenty-eighth Day of October, 2014

Michelle K. Lee
*Deputy Director of the United States Patent and Trademark Office*